US010295505B2

(12) United States Patent
Barbato et al.

(10) Patent No.: US 10,295,505 B2
(45) Date of Patent: May 21, 2019

(54) DEVICE FOR ULTRASOUND TESTS

(71) Applicants: Promedica Bioelectronics S.r.l., Rome (IT); Image Guided Therapy SA, Pessac (FR); Gaetano Barbato, Rome (IT)

(72) Inventors: Gaetano Barbato, Rome (IT); Nadia Catallo, Rome (IT); Cristiano Corso, Rome (IT); Gian Luca Scoarughi, Rome (IT); Erik Dumont, Pessac (FR)

(73) Assignees: PROMEDICA BIOELECTRONICS S.R.L., Rome (IT); IMAGE GUIDED THERAPY SA, Pessac (FR); BARBATO, GAETANO, Rome (IT)

( * ) Notice: Subject to any disclaimer, the term of this patent is extended or adjusted under 35 U.S.C. 154(b) by 118 days.

(21) Appl. No.: 15/112,831

(22) PCT Filed: Jan. 20, 2015

(86) PCT No.: PCT/IB2015/050434
§ 371 (c)(1),
(2) Date: Jul. 20, 2016

(87) PCT Pub. No.: WO2015/110955
PCT Pub. Date: Jul. 30, 2015

(65) Prior Publication Data
US 2016/0334373 A1 Nov. 17, 2016

(30) Foreign Application Priority Data

Jan. 21, 2014 (IT) .............................. RM2014A0031

(51) Int. Cl.
*G01N 29/27* (2006.01)
*C12M 1/42* (2006.01)
(Continued)

(52) U.S. Cl.
CPC ............ *G01N 29/27* (2013.01); *C12M 35/04* (2013.01); *G01N 29/222* (2013.01);
(Continued)

(58) Field of Classification Search
CPC .. G01N 29/27; G01N 33/4833; G01N 29/222; G01N 29/346; G01N 29/348; G01N 2291/02466; C12M 35/04
See application file for complete search history.

(56) References Cited

U.S. PATENT DOCUMENTS

2004/0173024 A1 9/2004 McKeon
2005/0212869 A1 9/2005 Ellson et al.
(Continued)

FOREIGN PATENT DOCUMENTS

WO 2007016605 A2 2/2007
WO 2009115523 A1 9/2009

*Primary Examiner* — Xin Y Zhong
(74) *Attorney, Agent, or Firm* — Volpe and Koenig, P.C.

(57) ABSTRACT

A device for ultrasound tests, includes one or more transducers for generating ultrasound beams with different powers/frequencies to be projected in direction of multiple targets, to ensure separate control of the temperature both of the targets and of the transducers and allows performing several tests contemporarily, by optimizing the functionality and the efficiency of the device, and guaranteeing results comparable therebetween for each test. The device also includes: a first supporting structure having at least a closed chamber receiving the transducer bodies and is isolated from a propagation liquid medium, by leaving exposed each respective vibrating surface in contact with the liquid medium at a prefixed distance from the respective targets, the closed chamber containing a thermorefrigerating fluid in contact with the body of the transducers; a second supporting structure for the targets; means for refrigerating the transducer bodies; and means for keeping the liquid medium at a predetermined temperature.

12 Claims, 3 Drawing Sheets

(51) Int. Cl.
*G01N 29/22* (2006.01)
*G01N 29/34* (2006.01)
*G01N 33/483* (2006.01)

(52) U.S. Cl.
CPC ......... *G01N 29/346* (2013.01); *G01N 29/348* (2013.01); *G01N 33/4833* (2013.01); *G01N 2291/02466* (2013.01)

(56) References Cited

U.S. PATENT DOCUMENTS

| | | | |
|---|---|---|---|
| 2006/0126884 A1* | 6/2006 | Hielscher | B06B 1/0611 381/397 |
| 2010/0009424 A1* | 1/2010 | Forde | C12M 23/50 435/173.4 |
| 2011/0011111 A1* | 1/2011 | Martin | G10K 11/004 62/259.2 |
| 2011/0177576 A1* | 7/2011 | Schaden | C12M 23/08 435/173.1 |
| 2012/0141552 A1* | 6/2012 | Dalecki | C12N 5/0062 424/400 |
| 2014/0038257 A1* | 2/2014 | Subramanian | C12N 13/00 435/173.8 |

\* cited by examiner

DEVICE FOR ULTRASOUND TESTS

The present invention has as subject a device for ultrasound tests, of the kind suitable to test the effect of ultrasounds with different intensities and frequencies on a plurality of targets.

Not for limitative purpose, an example of application of this type of device can be that of observing the interaction effect between ultrasounds and (prokaryotic and eukaryotic) cell cultures, or between ultrasounds and cell cultures wherein a drag has been inoculated, such as for example an antitumour drug on tumour cell cultures, with the purpose of verifying if the drug effectiveness increases the dosage being equal, or if the effectiveness thereof remains unaltered even if the dosage is decreased.

The ultrasounds are even used to induce the sonoporation of biological membranes, for translating nucleic acids, proteins, molecules or molecular aggregates, tracers (i.e. fluorescent markers, for Imaging with Magnetic Resonance etc.) inside cells by means of producing pores of the cell membranes, and to this purpose tests are required.

Then it is meant that several other applications of ultrasounds can be testes under strictly controlled conditions, even in fields different from isolated cell systems, such as for example in explanted or in vivo tissues, or in fields which lie outside of the strictly cell material.

A problem of general nature in performing this type of tests consists, on one side, in having to keep the targets at a predetermined temperature, constantly during the whole test and at the same time by keeping the transducers, which emit ultrasounds at a close distance thereto, at an adequate operating temperature, by means of a controlled cooling system, for the correct operation of the transducer but even to keep the emission of ultrasounds within parameters perfectly under control, with the purpose of making valid the performed test.

It is even meant that, with the purpose of being able to focalize correctly the ultrasounds emitted on the targets and avoid a dispersion thereof, the transducers have to be kept in a precise and possibly adjustable position with respect to the targets themselves.

Furthermore, another purpose that this invention intends to reach is that of allowing the exposition to ultrasounds of a plurality of targets, with the purpose of performing several tests contemporarily or in quick sequence, at the same time by allowing the not irradiated targets to remain stand-by at constant temperature and under optimum conditions.

The US patent application Nr. 2010/009424 A1 describes a device for inducing sonoporation, which however is unsuitable to perform diversified tests simultaneously.

On the contrary, the International patent application Nr. WO 2007/016605 describes an ultrasound device devised to interact on a plurality of targets, by keeping the transducers e the target at two different temperatures. The targets and the transducer are received in distinct portions of a same basin which are separated by a thermal insulating septum having, on an area below the target sample, an opening closed by a thin membrane which has the purpose of allowing the transmission of a beam of ultrasounds between such portions. This membrane cannot guarantee a sufficient thermal insulation, with consequent formation of a temperature gradient exactly in the sample area. Furthermore, the beam of ultrasound waves has to cross two liquid media which distinguish as they have different temperature, and this determines a different speed for propagating the sound and the acoustic impedance thereof in such liquid media, with consequent phenomena of reflection and partial refraction which prevent from precisely controlling the acoustic energy hitting the target.

It is meant then that this type of device can be used by renouncing to a regime of strict control of all operating parameters.

In the article "Ultrasound-Mediated Transfection of Mammalian Cells" by Hee Joong Kim et al., in HUMAN GENE TERAPY, 7:1339-1346 (July, 1996) another device is described able to make interacting a plurality of targets containing cell cultures with a beam of ultrasounds at two different frequencies, emitted thanks to two different transducers. In this apparatus, the ultrasound transducers are simply immersed in the basin containing the same liquid medium dampening even the targets. However, the emission of ultrasounds generates heat in the transducers, and it is eliminated during the operation thereof by means of the liquid which interposes close to the target sample. Then a thermal gradient is generated between the emitting surface of the transducers and that of the target. Even if there is a general system for controlling the basin temperature, it could not guarantee the necessary homogeneity of the temperature exactly at the route of the ultrasound beams, and a not homogeneous temperature inevitably influences the beam propagation by making it unstable and not controllable in a precise way.

Furthermore, this device, even if it has two transducers emitting ultrasounds at different frequency, positions them at the same distance from the target, since for the purposes the performed research sets the control of the positioning of the focal plane of the single transducers is not required. The technical problem of making to reach an iso-energetic acoustic wave intensity, even if at different frequency, is faced in a not structural way by the device. In fact, calibration measurements, preliminary to the experiment, must be carried out, performed by dipping a hydrophone in each sample by following a set of power calibration measurements, with consequent increase in laboriousness, the experiment time, and the risk of contaminating the sample.

In conclusion, this device then results to be unsuitable to scientific experiments to be performed in regime of strict control of all operating parameters.

The technical problem underlying the present invention is to provide a test device for ultrasounds allowing to obviate to the drawbacks mentioned with reference to the known art.

Such problem is solved by a device as above specified, defined in the enclosed claim 1.

The main advantage of the device according to the present invention lies in guaranteeing the projection of different beams of ultrasounds on a plurality of targets, the temperature thereof, together with that of the ultrasound transducers, are kept under strict control independently one with respect to the other one.

The possible presence of several transducers and of a plurality of targets further allows to perform several tests contemporarily, by optimizing the functionality and the efficiency of the test device, at the same time by guaranteeing results comparable therebetween for each test.

The present invention will be described hereinafter according to two preferred embodiments thereof, provided by way of example and not for limitative purpose with reference to the enclosed drawings wherein.

Figure 1:
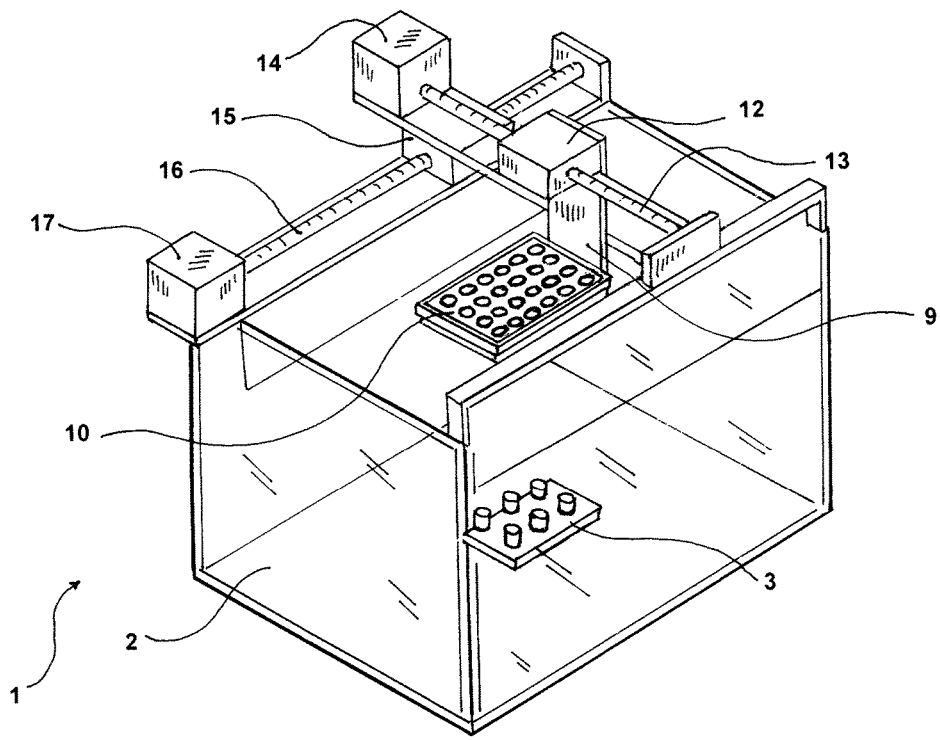
FIG. 1 shows a perspective view of a first embodiment example of a test device according to the present invention.
Figure 2:
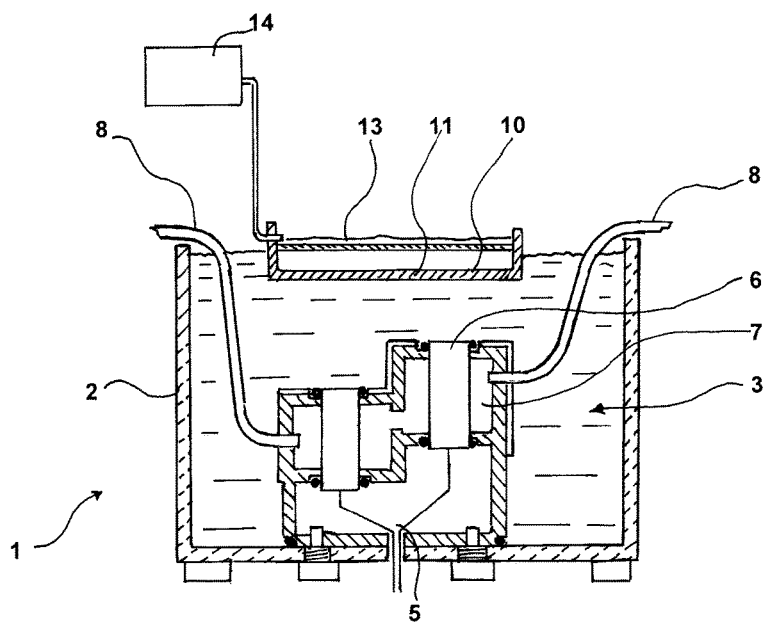
FIG. 2 shows a raised and section view of the test device of FIG. 1.

With reference to the figures from 1 to 3A, a test device for ultrasound applications to specific targets is designated as a whole with 1.

It comprises a container 2, substantially a basin, delimitated by a bottom and by side walls. The container is filled up with a fluid, in particular distilled water, the temperature thereof is kept under strict control. Such fluid constitutes a liquid medium which is used for the propagation of an ultrasound beam as it will be explained in details hereinafter.

As far as the transmission of ultrasound is concerned, the fluid is degassed and means for degassing this fluid can be provided.

In the present embodiment example the container 2 is implemented by a basin with side walls in glass (or plastic or metallic material), wholly filled up with water; this, in case of transparent glass or plastic material, allows the direct vision of the basin content.

From a thermal point of view, the water mass constitutes a relevant thermal inertia with respect to the masses of the other existing components; means for keeping such fluid at a prefixed and controlled temperature is provided, in particular a constant temperature selected based upon the targets to be treated.

Such means for keeping the temperature can comprise means to make the fluid to circulate outside the container 2 wherein a thermostat will be provided; otherwise, the thermostat, for example of the type with electric resistances, could be dipped directly into the container in direct contact with the fluid.

Means for agitating the fluid inside the container 2 could be provided, to prevent stagnations and stratifications of fluid with different temperatures, as well as instruments for controlling the temperature in one or more sites of the container 2.

The device 1 comprises a first supporting structure 3 for a number of the transducers 4 apt to generate each one an ultrasound beam. Such transducers could be of the piezoelectric type, fed by a control room with electric current, that is a multiple radiofrequency signal, with adequate frequency and power.

Each transducer 4 comprises a transducer body, containing the material to dampen the vibration and dissipate the heat, and which ends with a vibrating surface which will have to interface with said liquid medium, so as to be dampened to allow the direct propagation of an ultrasound beam to targets which, in turn, will be dampened by the liquid medium.

This type of the transducers 4, in order to be able to offer an adequate operation in terms of efficiency, must have its own transducer body kept at a controlled temperature involving a continuous refrigeration. In fact a temperature variation above a critical temperature not only can determine an operative sufferance of the transducer, but can even make unstable the generation of ultrasounds.

In the present example, the transducers are of cylindrical type with a plane vibrating surface generating the ultrasound beam, made of piezo-ceramic material and protected by a metallic casing; the vibrating transduction surface, is in direct contact with a solid material body suitable to an effective thermal dispersion by contact.

The working frequencies, in case of using four transducers, will be 650 kHz, 1 MHz, 2.4 MHz, and 4.5 MHz, but it underlines that both the choice of having a solid material body and the choice of the number of the transducers and of the specific frequencies are purely exemplifying.

Furthermore, for specific applications, even transducers of spherical type, or however able to generate a waveform of the wished shape, can be used.

The frequencies are chosen to cover a wide range, to be able to implement different types of experiment, by avoiding overlapping of upper harmonics of each frequency which could introduce unwished disturbances.

It is to be known that the vibrating surface of the transducer is exposed to the fluid contained in the container 2; the transducer body has to be kept at a temperature of 10-15° C., whereas a typical predetermined temperature of the propagation liquid medium is 37° C.

Each transducer body is equipped with a thermocouple for controlling its temperature, which constitutes means for detecting the temperature of each transducer 4.

Figure 3:
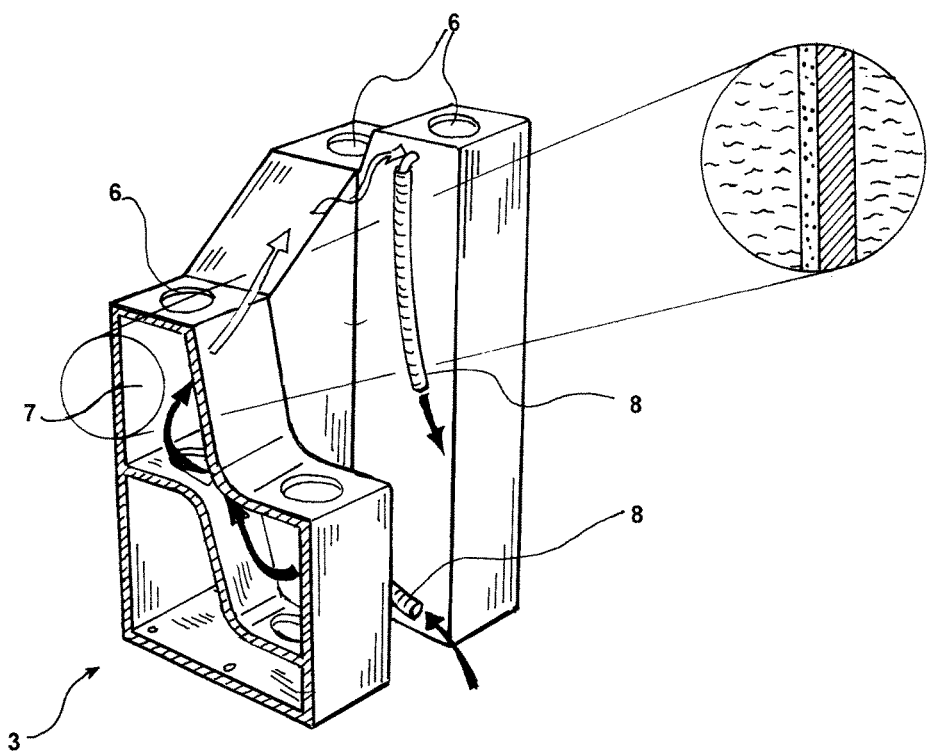
FIG. 3 shows a perspective and partially section view of a component of the test device of FIG. 1, with an additional enlarged detail.
Figure 3A:
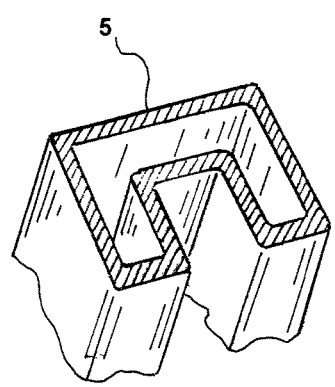
FIG. 3A shows a perspective view from the pitch of another detail of the component of the previous figure.

The first supporting structure 3 according to a first embodiment example is of box-like type; it comprises a basement 5 (FIG. 3A) apt to be fixed on the bottom of said container 2. Inside the structure 3 different seats 6 are formed receiving each one a respective ultrasound transducer; said seats 6 belong to a single close chamber 7, thermally isolated with respect to said liquid medium of the basin and wholly enclosed inside the first supporting structure 3. Such chamber 7 is filled up with thermorefrigerating fluid, in the present example again water, which advantageously is made to flow to determine a forced convection in the fluid touching each transducer, so as to keep the ultrasound generator below a critical temperature.

The thermorefrigerating fluid circulates in said chamber 7 from suitable ducts 8 crossing the container 2 and transporting the fluid to a suitable refrigerating thermostation, which keeps the refrigerating water at a temperature of about 10-15° C.

It is to be noted that said seats 6 in the first supporting structure 3 are step-like arranged so as to keep the respective transducer at a specific height characteristic of the transducer, in order to obtain a determined acoustic field at the target position.

The seats, in case of four transducers, are arranged according to a square matrix 2×2. The number of the transducers can even be different from four, to cover with different frequencies an overall wide range. Applications with one, two or three transducers, in case arranged in line, or six transducers arranged on a rectangular matrix 2×3 can be provided. The number of the transducers could be even higher than 6, but they could be redundant if each one worked at a different frequency. Another embodiment could use eight transducers divided into two equal square matrixes 2×2, so as to have two equal groups operating contemporarily.

The transducers 4 are driven by an electric signal which makes a sheet/lamina to vibrate in said composite piezo-ceramic material. An impedance coupler balances the inner impedance of the transducers to the output impedance of the generator of the radiofrequency signal used to drive the transducers, so as to maximize the transferred power.

The different signals are controlled by a suitable control room constituting means to vary said power and/or frequency of beam of ultrasounds emitted by each transducer within a specific range characteristic of each transducer.

The device 1 comprises a second supporting structure 10 of a plurality of the targets designated each one with 11.

The second supporting structure 10 substantially comprises a tray with seats forming a matrix of the targets, for example 4×6=24 different targets. For example, the target could be a traditional plate for cell cultures with 24 wells.

Advantageously, the targets are arranged according to a plane matrix in a multiple number of the number of the transducers, in this example 24 (4×6) vs 6 (2×3). Furthermore, the distances between the centres of the adjacent transducers will be multiple of the distances between the centres of the adjacent targets.

In this way, to change the targets irradiated by the matrix of the transducers, it will be sufficient to translate the ones or the other ones by the distance between the targets according to axes perpendicular therebetween. This simple translation of one or more pitches, wherein under pitch exactly the minimum distance between the targets is meant, will allow arranging contemporarily all transducers in front of new targets.

Each target 11 is constituted by a well made of very thin plastic material which has a substantially glass-like shape, which is dampened by the liquid medium of the basin. To this purpose, the bottom of the well is wholly dipped in the fluid contained in the container 2, so as to be even in thermal contact therewith.

The well contains a solution receiving, in this example, a cell culture: reduced thicknesses of the well wall allow minimizing possible diffraction phenomena.

In this example, the cultures could be kept at an almost constant pressure of 37° (or other suitable temperature) during all tests, both during the irradiation and during the stand-by periods before and after the tests.

In this way, the previously described means to keep constant the temperature of the thermorefrigerating fluid in the container 2 constitutes even means to keep said targets at a constant temperature.

By considering the flat tray-like shape of the second supporting structure 10, all targets can be kept at the same height which will correspond substantially to that of the focal plane of the transducers 4, if one wishes to centre identically the focus of each transducer inside the well. Alternatively, if one wishes to make to act the so-called near field or far field one can act by positioning properly the plane of the supporting structure 10 at a different height along the axis Z, so as to lower or raise, respectively, the position of the tray plane with respect to the focal plane.

It is to be noted to this purpose that, by considering the different distances of each transducer 4, they could be driven not only at different frequencies but even at different power, so that on each target a constant power (or an equal acoustic pressure) can be applied for a predetermined period of time, by making the various tests comparable therebetween.

By way of example, by considering the previously mentioned typical frequencies, and the implementation conditions providing a fluid with constant T of 37° C. and a flat vibrating element of the transducer with diameter of 12.00 mm, the distances between the flat surfaces of each transducer and the focal plane will be the following:

| Frequency | Focal distance |
|---|---|
| 650 kHz | 15.38 mm |
| 1 MHz | 23.68 mm |
| 2.4 MHz | 57.14 mm |
| 4.5 MHz | 105.88 mm |

It is to be noted that with the above-mentioned frequencies the transducers 4 can be driven on frequencies so as to cover the whole range characteristic of these acoustic waves, by keeping the efficiency of each transducer 4 however higher than 50%.

In order to implement the motions of the above-described targets, the second supporting structure comprises first means for translating the targets on the focal plane common to said transducers 4 along two possibly perpendicular directions, or axes lying on such plane.

To this purpose, the tray is supported by an arm 9 connected to a first cursor 12 assembled along a first screw shaft 13 driven by a first electric motor 14, in turn assembled on a second cursor 15 assembled along a second screw shaft 16 driven by a second electric motor 17, with the screw shafts perpendicular therebetween.

In the present example, even the arm 9 allows a vertical translation perpendicular to the focal plane, to allow manoeuvring the tray of the second supporting structure 10 or for fine adjustments of the focal distances. Thus it constitutes second means for translating the targets in a direction parallel to the propagation of the ultrasound beam, to arrange the targets in the near field or far field of the ultrasounds, and/or in a vertical direction of moving away from the first supporting structure 3, according to the correct focal distance of the transducer 4 which is made operating in the system. It is to be meant that preferably said directions coincide.

Therefore, the first means for translating the targets move said matrix along two perpendicular axes with pitches corresponding to the minimum distance between the targets in said matrix, as described previously.

It will be understood that it could be convenient even using plates with matrixes with different sizes, for example larger ones, with 48 targets (4×12 or 6×8) or 96 targets (6×16 or 8×12).

Figure 4:
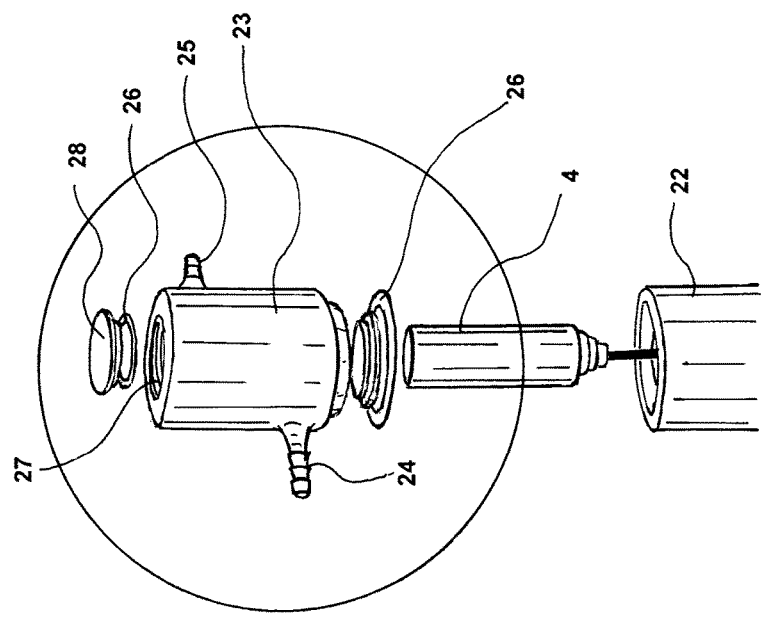
FIG. 4 shows a perspective view with some underlined details of a variant of the component shown in FIG. 3, which implements a second embodiment example of the test device according to the invention.
Figure 4:
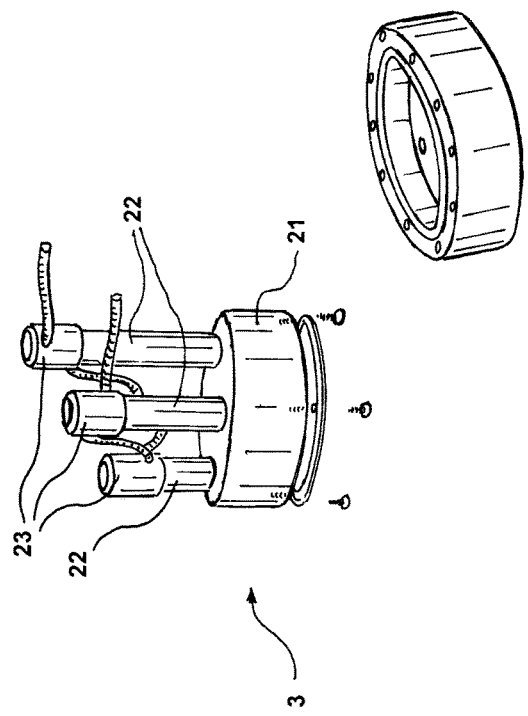

By referring to FIG. 4, an alternative embodiment of the first supporting structure implementing a second embodiment example of the test device according to the invention is described.

It comprises a basement 21 therefrom tubular supports 22 project sustaining, each one, a transducer 4 at a certain characteristic height on their own top. It comprises a containment 23 for each transducer defining a respective closed chamber of the transducer body, with a jacket surrounding the transducer body for the adequate cooling thereof.

Each tubular support 22 is then fed by respective inlet lines 24 and outlet lines 25, transporting a thermorefrigerating fluid with the previously described function.

On its own upper face, each containment 23 comprises a hole 27 exposing the flat vibrating surface of the top of the transducer 4 containing the vibrating element made of composite piezo-ceramic material. It is kept by means of screwing the ferrule 28 squeezing the gasket 26 by guaranteeing the sealing of the whole compartment. It is to be noted that the distance thereat the transducers are placed from the respective coplanar targets could even be constant, with the purpose of differentiating, instead of the frequencies, the intensity of the ultrasound beams.

To this purpose, the test device could have available two or more different supporting structure for transducers: one at differentiated heights and one or more at constant heights, corresponding to a specific operating frequency.

Advantageously, a single first supporting structure could be used equipped with means for translating vertically each transducer separately from the other ones, thus obtaining the maximum operating flexibility in the same test device.

By way of example, a similar solution could be integrated inside the tubular supports described by referring to the second embodiment example.

A person skilled in the art, in order to satisfy additional and contingent needs, can introduce several additional modifications and variants, all however within the protective scope of the present invention, as defined by the enclosed claims.

The invention claimed is:

1. A device for ultrasound tests, comprising ultrasound transducers for generating ultrasound beams with different powers and/or frequencies to be projected in direction of a plurality of targets (11) through a liquid medium, the device comprising:
a container having walls and a bottom, filled with said liquid medium;
a first supporting structure for one or more ultrasound transducers, fixed on the bottom of said container, seats for said one or more ultrasound transducers being formed therein, each seat receiving a respective ultrasound transducer, the first supporting structure having at least one closed chamber isolated from said liquid medium and receiving said one or more ultrasound transducers, so as to leave exposed respective vibrating surfaces thereof, in contact with said liquid medium, the closed chamber containing a thermorefrigerating fluid in contact with said one or more transducers;
a second supporting structure for said targets comprising a plurality of wells kept at a prefixed distance from said vibrating surfaces, said wells having a bottom wholly clipped in the liquid medium, to be in thermal contact therewith;
means for refrigerating, through said thermorefrigerating fluid, the body of said one or more transducers; and
means for keeping the liquid medium, dampening said targets, at a predetermined temperature.

2. The device for ultrasound tests according to claim 1, wherein said second supporting structure for said targets has first means for translating the targets along two axes defining a horizontal plane corresponding to a focal plane of said one or more transducers.

3. The device for ultrasound tests according to claim 1, wherein the targets are arranged in a matrix in a multiple number of the number of said transducers, also arranged in a matrix, the distances between centers of adjacent transducers being multiple of the distances between centers of adjacent targets.

4. The device for ultrasound tests according to claim 1, wherein means for varying said power and/or frequency of the beam of ultrasounds emitted by each transducer within a specific range characteristic of each transducer is provided.

5. The device for ultrasound tests according to claim 2, further comprising second means for translating the targets along an axis parallel to the direction of propagation of the ultrasound beam, in order to move the targets in the near field or far field of the respective focal plane.

6. The device for ultrasound tests according to claim 2, wherein said one or more ultrasound transducers comprises a plurality of ultrasound transducers, the first supporting structure defines for each ultrasound transducer, a different distance from the focal plane thereon the targets are arranged, which substantially corresponds to the focal distance for the frequency generated by the ultrasound transducer, the device further comprising second means for translating the targets along a vertical axis, parallel to the direction of propagation of the ultrasound waves, so as to place the targets at the focal plane of each respective transducer.

7. The device for ultrasound tests according to claim 1, wherein said means for refrigerating said one or more ultrasound transducers comprises means for detecting the temperature of each ultrasound transducer (4).

8. The device for ultrasound tests according to claim 1, wherein said first supporting structure is box-like and comprises therein different seats, each one configured to receive a respective ultrasound transducer, said seats implementing a single closed chamber, inside said first supporting structure filled up with a thermorefrigerating fluid which is made to flow inside the chamber to determine a forced convection by touching each transducer.

9. The device for ultrasound tests according to claim 8, wherein said seats are step-like arranged so as to keep each transducer at a respective characteristic height.

10. The device for ultrasound tests according to claim 1, wherein said first supporting structure comprises a basement wherein a plurality of tubular supports project vertically therefrom each tubular support sustaining a transducer at a characteristic height on a top portion thereof, each tubular support comprising a respective containment, for a corresponding ultrasound transducer, which defines a respective closed chamber and which has a jacket surrounding the ultrasound transducer, the containment being fed with thermorefrigerating fluid through respective inlet lines and outlet lines, on the upper face of each tubular support being provided a respective hole exposing said vibrating surface of the ultrasound transducer to said liquid medium, and a ferrule guaranteeing the sealing by squeezing a gasket.

11. The device for ultrasound tests according to claim 1, wherein said first supporting structure is equipped with additional means for translating each single ultrasound transducer vertically.

12. The device for ultrasound tests according to claim 1, further comprising means for stirring the fluid inside the container and instruments for controlling the temperature in one or more sites of the container.

* * * * *

UNITED STATES PATENT AND TRADEMARK OFFICE
CERTIFICATE OF CORRECTION

PATENT NO. : 10,295,505 B2
APPLICATION NO. : 15/112831
DATED : May 21, 2019
INVENTOR(S) : Gaetano Barbato et al.

It is certified that error appears in the above-identified patent and that said Letters Patent is hereby corrected as shown below:

In the Claims

In Claim 1, Column 7, Line 31, delete the word "clipped" and insert the word --dipped--.

Signed and Sealed this
Ninth Day of July, 2019

Andrei Iancu
*Director of the United States Patent and Trademark Office*